(12) United States Patent
Mikheev et al.

(10) Patent No.: US 8,515,200 B2
(45) Date of Patent: Aug. 20, 2013

(54) SYSTEM, SOFTWARE ARRANGEMENT AND METHOD FOR SEGMENTING AN IMAGE

(75) Inventors: Artem Mikheev, New York, NY (US); Henry Rusinek, Great Neck, NY (US)

(73) Assignee: New York University, New York, NY (US)

( * ) Notice: Subject to any disclaimer, the term of this patent is extended or adjusted under 35 U.S.C. 154(b) by 1471 days.

(21) Appl. No.: 11/264,775

(22) Filed: Oct. 31, 2005

(65) Prior Publication Data

US 2006/0094961 A1 May 4, 2006

Related U.S. Application Data

(60) Provisional application No. 60/623,840, filed on Oct. 29, 2004.

(51) Int. Cl.
*G06K 9/42* (2006.01)
*G06K 9/00* (2006.01)

(52) U.S. Cl.
USPC ............................. 382/256; 382/128; 382/173

(58) Field of Classification Search
USPC .......... 382/173, 254, 255, 256, 128; 600/437
See application file for complete search history.

(56) References Cited

U.S. PATENT DOCUMENTS

| | | | |
|---|---|---|---|
| 6,775,401 B2 * | 8/2004 | Hwang et al. ................ | 382/131 |
| 6,898,302 B1 | 5/2005 | Brummer | |
| 2003/0223627 A1 * | 12/2003 | Yoshida et al. ............... | 382/128 |

OTHER PUBLICATIONS

Kaschwich et al., "Wavefront-Oriented Ray Tracing in 3D Anisotropic Media," Jun. 2-5, 2003, EAGE 65rd conference & Exhibition, pp. 1-4.*
Anoraganingrum, "Cell Segmentation with Median Filter and Mathematical Morphology Operation," 1999, IEEE, pp. 1043-1046.*
Shibolet, "Coloring Voxel-based Objects for Virtual Endoscopy," Oct. 24, 1998, IEEE, pp. 15-22.*
Macari, Michael et al. "Colorectal Polyps and Cancers in Asymptomatic Average-Risk Patients: Evaluation with CT Colonography", Radiology 2004, vol. 230, pp. 629-636.
Johnson, C. Daniel et al. "CT Colonography: The Next Colon Screening Examination?", Radiology 2000, vol. 216, pp. 331-341.
Zalis, Michael E. et al. "CT Colonography: Digital Subtraction Bowel Cleansing with Mucosal Reconstruction—Initial Observations", Radiology 2003, vol. 226, pp. 911-917.
T. Kaschwich et al. "A Wavefront-Oriented Ray Tracing in 3D Anisotropic Media," EAGE 65rd Conference & Exhibition—Stavanger, Norway, Jun. 2-5, 2003.

* cited by examiner

*Primary Examiner* — John Strege
(74) *Attorney, Agent, or Firm* — Dorsey & Whitney LLP

(57) ABSTRACT

A logic arrangement, system and method for segmentation using magnetic resonance imaging ("MRI") are provided. For example, as an end product, an image associated with at least one portion of an anatomical structure is generated. In particular, first data associated with the at least one portion of the anatomical structure is received. Second data can be associated with at least one edge of at least one of the at least one portion is obtained based on the first data. The image can be generated based on the first data and the second data. In addition or as an alternative, it is also possible to generate the image using connected voxel components. Such components are created by processing information associated with an erosion of surface voxels of an image.

69 Claims, 5 Drawing Sheets

Fig. 7(a)
Fig. 7(b)
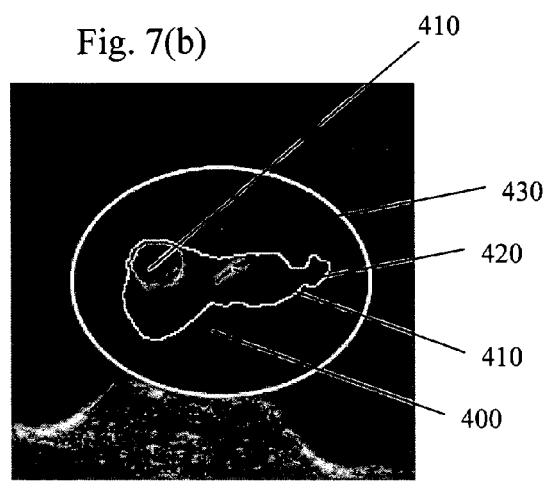
Fig. 8(a)
Fig. 8(b)
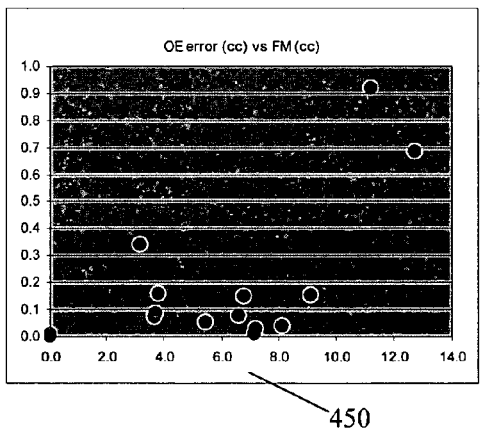
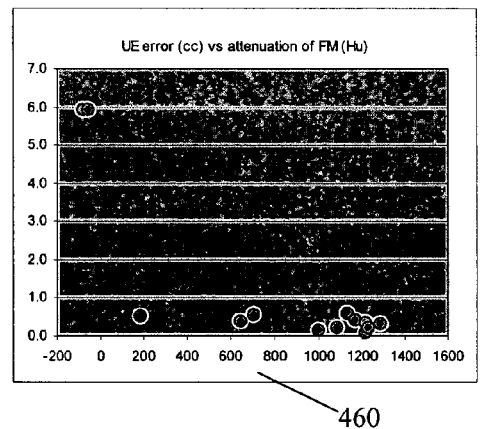

SYSTEM, SOFTWARE ARRANGEMENT AND METHOD FOR SEGMENTING AN IMAGE

CROSS-REFERENCE TO RELATED APPLICATION(S)

This application claims priority from U.S. patent application No. 60/623,840, filed on Oct. 29, 2004, the entire disclosure of which is incorporated herein by reference.

FIELD OF THE INVENTION

The present invention relates generally to imaging software arrangements, methods and systems, which can use magnetic resonance ("MR"), computed tomography (CT), and/or any other imaging techniques. In particular the present invention relates to software arrangements, methods for image segmentation from magnetic resonance imaging ("MRI"), and to systems and software arrangements utilizing such methods.

BACKGROUND INFORMATION

Magnetic Resonance Imaging ("MRI") systems generally use strong magnetic fields in order to polarize the magnetic spins of nuclei to be imaged, and to create the magnetic resonance condition therein.

Numerous clinical and research applications related to brain imaging using MRI, Computerized Tomography ("CT"), Positron Emission Tomography ("PET"), and Single Proton Emission Computerized Tomography ("SPECT") require the ability to accurately extract the brain tissue from the image data. For example, for patients suffering from various brain disorders (such as traumatic injury, multiple sclerosis, or dementia), brain atrophy estimation, the rate of atrophy (the difference in brain volume at two points in time) and brain shape itself can provide important diagnostic information. Imaging parameters can be more sensitive and consistent measures of disease progression than cognitive assessment in patients with Alzheimer's disease. Imaging measures may be used to predict the course of disease and could be used as surrogate endpoints in treatment.

In addition to imaging of the brain, Magnetic Resonance ("MR") and CT images of the head contain non-brain elements such as bone, skin, fat, muscle, and eyeballs. Multi-modality algorithms generally require that these non-brain parts of the image be removed before registration.

A segmentation of the brain tissue is one of the most time-consuming preprocessing steps performed in neuro-imaging laboratories. A number of brain extraction algorithms have been developed to perform this step automatically. Such conventional algorithms may generally enhance the speed of overall image processing, but still have various drawbacks.

One such conventional technique and system, i.e., Brain Extraction Tool ("BET"), utilizes an intensity based estimation of the brain-non-brain threshold, determines the center of gravity of the head, defines a starting sphere based on the center of gravity, and deforms the tessellated sphere outward toward the brain surface. Similarly to any intensity-only based method, the drawback of this conventional approach is low accuracy.

Another conventional technique and system, i.e., Brain Surface Extraction ("BSE"), utilizes an edge-based method based on an anisotropic diffusion filtering technique. The edge detection can be implemented using a 2D Marr-Hildreth operator. The final step of BSE includes morphological processing of the edge map. The drawback to such BSE approach is generally poor precision. Further, using a 2D edge detector on 3D data generally provides little benefit, since such algorithm may not exploit the correlation of edges across adjacent slices.

A further conventional technique and system, i.e., Minneapolis Consensus Strip ("McStrip"), is an iterative combination of the above two approaches. According to this procedure, the target mask is formed by the BET approach, and then an exhaustive search is performed to obtain the parameters of BSE that provide a BSE mask that is closest to the BET mask. Due, in part, to the iterative nature of this technique, the execution time of such approach generally makes it unsuitable for a routine use, even though there may be a good the precision.

Now, addressing traditional methods of colorectal screening, it has been previously discussed that the majority, e.g., 85-90%, of colorectal cancers progress through the benign adenoma-Carcinoma sequence, with an average of 5.5 years required for the transformation of a large adenomatous polyp into cancer. Colon cancer screening can decrease the mortality of colorectal cancer by identifying these pre-malignant lesions. Screening has been shown to decrease the morbidity and mortality by detecting and removal of pre-malignant adenomatous polyps. There is consensus among health care providers and policy makers that screening for colorectal cancer is justified. The conventional options available for colorectal carcinoma screening include digital rectal examination, fecal occult blood testing, sigmoidoscopy, double contrast barium enema, and fiberoptic colonoscopy.

Despite the consensus on the need and efficacy of screening, there are about 150,000 new cases and 60,000 deaths from colon cancer every year in the United States. Since screening can detect the precancerous adenomas, the continued high prevalence of colon cancer is alarming. Only 17.3% of patients over age 50 had undergone fecal occult blood testing within the last year and 9.4% had undergone sigmoidoscopy within the last three years. However, conventional colon screening options have important limitations. For example, fecal blood test does not directly evaluate the colonic mucosa. Many large adenomatous polyps and cancers do not bleed. In more than 50% of occult home positive stool examinations, the source of blood was from the upper gastrointestinal tract. Screening sigmoidoscopy generally fails to evaluate the entire colon, may miss many advanced proximal carcinomas. The sensitivity of barium enema examination in detecting polyps larger than 5 mm is only about 25% and 50% for polyps greater than 1 cm.

Complete fiber-optic colonoscopy allows for a thorough evaluation of the colon, and has the added benefit of biopsy or excision of suspicious lesions. However, there are several important limitations to the widespread use of screening colonoscopy including need for sedation, potential risk of perforation and bleeding, costs of the procedure including the need for sedation, failure to complete the examination in 5-10% of patients, and an insufficient workforce of trained endoscopists to meet the demand (15,16). One of important limitation of conventional colonoscopy is that in order to perform the examination, the colon must be thoroughly cleansed of residual fecal material. This is typically performed with polyethylene-glycol-solutions or phospho-soda preparations. Patients find bowel cleansing the most difficult aspect of screening, whether sigmoidoscopy, DCBE, or colonoscopy is used.

CT colonography ("CTC") is an imaging technique for colorectal polyp detection that relies on performing thin sections computed tomography ("CT") of the colon, and has been described in various publications. Preliminary clinical evaluation of CTC shows positive results in detecting polyps and cancers of the colon and rectum, with sensitivity values ranging from 75-100% for polyps that are at least 10 mm. CT and conventional colonoscopy has been evaluated for the detection of polyps in asymptomatic, average risk, patients. (See M. Makari et al., "Colorectal Polyps and Cancers in Asymptomatic Average-Risk Patients: Evaluation with CT Colonography," Radiology 2004, Vol. 230, pp. 629-636.) It is suggested that CTC may be an accurate study in detecting clinically significant colorectal lesions in a screening population. The mean interpretation time may be about 9 minutes. Interpretation times in this range are important if CTC is to be used as a widespread screening tool. Studies evaluating patient preferences have shown CT colonography to be preferred over conventional colonoscopy. Data has shown that 70.5% of patients preferred CTC over conventional colonoscopy. However, the current CTC data are acquired after colonic cleansing for optimal data interpretation. Bowel cleansing may be a major impediment to widespread CTC, it is judged uncomfortable (e.g., by about 89% of patients) and inconvenient (e.g., by about 78% of patients). By eliminating the need for bowel cleansing, patient and physician acceptance of CTC as a colon cancer screening tool would likely substantially increase. If CTC was effective in detecting colorectal polyps, and did not require a bowel preparation, it could become the colorectal cancer screening test of choice.

Given the limitations of current bowel preparations, including poor patient compliance as well as residual fecal material that can make interpretation difficult, the possibility of fecal and fluid tagging for CTC has been investigated. Fecal tagging without bowel cleansing relies on having the patient ingest small amounts of dilute barium with low fat and fiber diets one to several days prior to the examination. When the CT examination is performed, residual fecal material that is tagged may have high attenuation and appear brighter on the image. If there are large amounts of residual "tagged" fecal material present, clinically significant polyps could be obscured. Utilizing segmentation techniques it is possible to remove tagged fecal material leaving only the colonic mucosa, polyps, and colorectal neoplasms.

Several studies evaluated fecal tagging. The software for implementing such technique is based on replacing CT pixels with attenuation greater than 200 HU with "air" (−1,000 HU), followed by selective smoothing of a 3-pixel-thick transition layer at the bowel wall-air interface. (See M E Zalis et al., "CT Colonography: digital subtraction bowel cleansing with mucosal reconstruction-initial observations," Radiology 2003, Vol. 226, pp. 911-917). If a polyp is surrounded by residual fecal material, this software modifies a 2 mm thick surface layer of the polyp. This is an undesirable side effect. Moreover, a purely threshold-based technique is clearly unable to remove incompletely tagged fecal matter. This is a limitation, since despite the best effort to tag fecal material, there are always be some poorly or partially tagged fecal matter remaining. Thus, a need exists to provide techniques to remove both tagged and untagged fecal matter from the colon.

Therefore, there is a need to be able to perform a segmentation of brain tissue and of other biological matter with a high precision and a relatively short execution time.

OBJECTS AND SUMMARY OF THE INVENTION

One of the objects of the present invention is to overcome at least some of the aforementioned problems and deficiencies. For example, in an exemplary embodiment of the method, software arrangement and system according to the present invention, the segmentation referenced above can be accomplished using edge constrained peel/grow technique with a spherical wavefront approximation.

For example Peel and Grow operations techniques may be important operations an exemplary algorithm according to the present invention which is used by the software arrangement, system and method. Such operations may share substantially identical algorithmic description. The algorithm is applicable for both 2-dimensional and 3-dimensional cases, as well as higher dimensions if necessary. The description of 3D variant may also be relevant to the practical applications of this exemplary algorithm according to the present invention.

The input data of the algorithm may be presented as a 3D matrix of labels. The matrix can have dimensions of W×H×D (i.e., Width, Height, and Depth, respectively).

Although each label can be of any bit length, according to one exemplary embodiment, BYTE (8-bit) labels may be used. Each label can also be interpreted as an isotropic vertex of the voxel. Each voxel of the original volume can have 8 vertexes. These vertexes form a cube with the sides of length "1" in three dimensions. This minimizes amount of data to be accessed during the processing of the algorithm, while simplifying the access to individual labels, thus resulting in a robust performance.

An exemplary embodiment of the present invention utilizes a 26-neighbor connectivity model. For example, vertex of the isotropic 3d lattice may have exactly 26 neighbors. Each neighbor has a different distance from the parent. In the three-dimensional case, possible distances may be 1 unit, which can equal to a spacing of the isotropic 3d lattice, the square root of 2, and the square root of 3 (based on the distance from vertex to vertex in the cube arrangement). The wavefront propagation algorithm which can be used according to the present invention can take into account those differences, thus facilitating a better approximation of an ideal spherical wavefront than conventional algorithms, because, e.g., because the difference between various spatial directions may be smaller. In addition, a user is able to specify a fractional number (e.g., in voxels) of Peels. Fractional numbers generally provide a better discrimination power in the practical applications, for example, when the critical organ dimension to be imaged is very small (e.g., the thickness of a colon fold can be somewhere between 1-2 voxels).

Further, the wavefront according to an exemplary embodiment of the present invention can be propagated through voxel vertex. This allows a resolution of certain edge-related contradictions, which may not have been possible under conventional voxel propagation models.

According to an exemplary embodiment of the present invention, a logic arrangement, system and method for segmentation using magnetic resonance imaging ("MRI") are provided. For example, as an end product, an image associated with at least one portion of an anatomical structure is generated. In particular, first data associated with the at least one portion of the anatomical structure is received. Second data can be associated with edges obtained from the first data. The image can be generated based on the first data and the second data. In addition or as an alternative, it is also possible to generate the image using connected voxel components. Such components are created by processing information associated with an erosion of surface voxels of an image.

According to another exemplary embodiment of the present invention, third data can be provided that is associated with a volume of a soft tissue of the portion based on the first data; and the second data may be with the third data to obtain fourth data. In this manner, it is possible to separate anatomically distinct and adjacent sections of the at least one portion from one another. The image may be generated further based on the fourth data. The third data may include information regarding surface voxels associated with the portion. Further data associated with the surface voxels can be processed so as to generate connected voxel components. In this manner, the image can be generated further based on the connected voxel components. In addition, the surface voxel can be eroded morphologically, and the connected voxel components may be ordered according sizes thereof.

In still another exemplary embodiment of the present invention, the voxel components can be grown so as to offset the processing of the voxels associated with the portion. The voxel components may be grown using a wavefront propagation technique. Voxels can be added that are part of the third data to the voxel components. Data masks may be generated for separate connected bodies of the at least one portion, and the connected bodies that are smaller in size than a predetermined threshold can be removed so as to provide at least one resultant body. The image may be generated further based on the at least one resultant body.

According to yet another exemplary embodiment of the present invention, further data associated with a volume of a soft tissue of the portion may be generated based on the first data. The further data may include information regarding surface voxels associated with the portion. Further, information associated with an erosion of the surface voxels may be processed so as to generate connected voxel components, and the image can be generated further based on the connected voxel components.

BRIEF DESCRIPTION OF THE DRAWINGS

FIG. 7(a) is an exemplary image of an exemplary slice of a colon;

FIG. 7(b) is an exemplary image of the colon shown in FIG. 7(a), which includes areas of interest that are marked for use with the exemplary embodiment of the present invention;

FIG. 8(a) is a exemplary graph illustrating an over-segmentation error in 20 colon-segments;

FIG. 8(b) is a exemplary graph illustrating an under-segmentation error plotted as a function of an attenuation of a fecal material ("FM");

Figure 1:
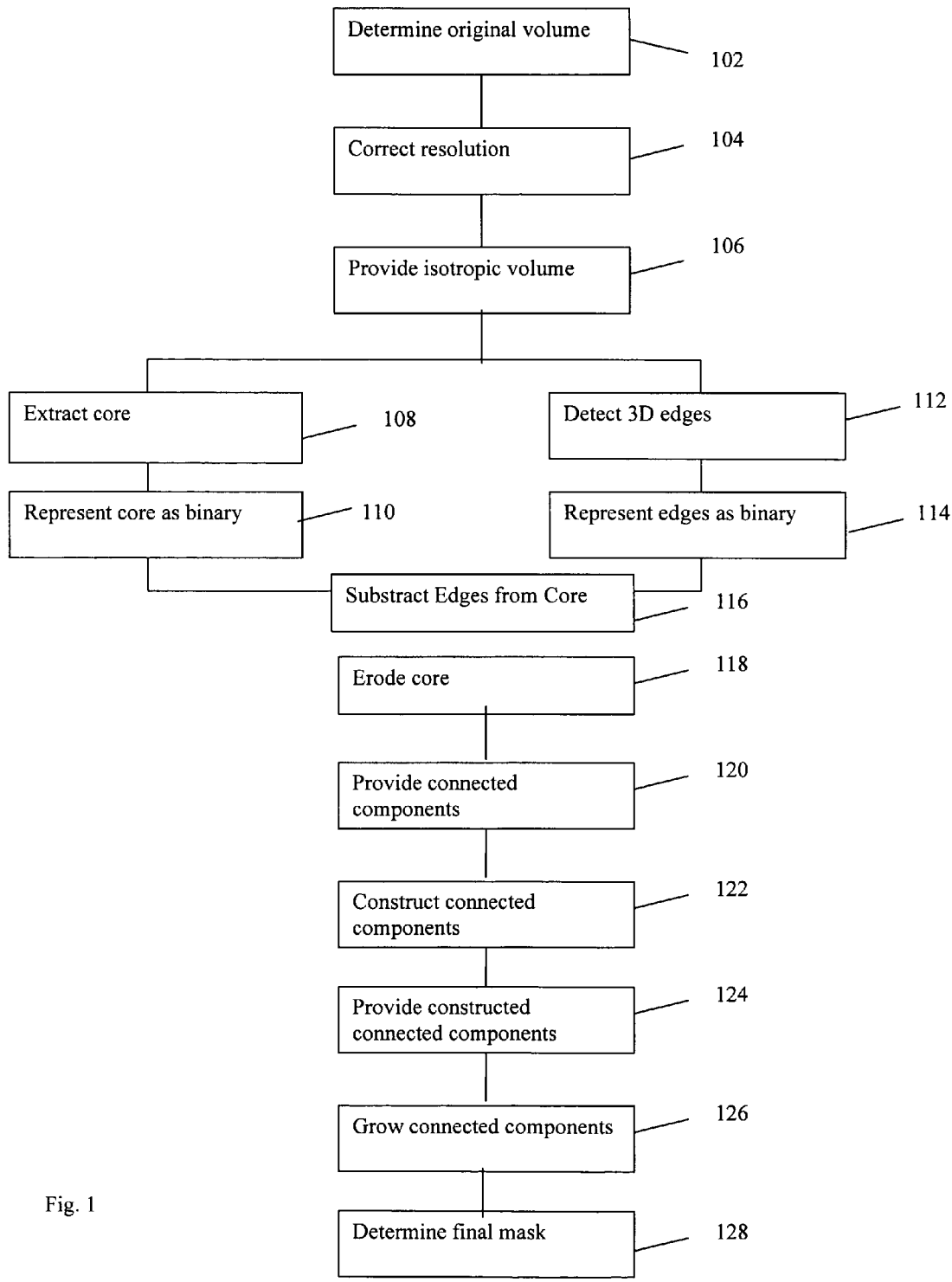
FIG. 1 is a flow diagram of an exemplary segmentation procedure according to an exemplary embodiment of the present invention.

Throughout the figures, the same reference numerals and characters, unless otherwise stated, are used to denote like features, elements, components or portions of the illustrated embodiments. Moreover, while the present invention will now be described in detail with reference to the figures, it is done so in connection with the illustrative embodiments.

DETAILED DESCRIPTION

FIG. 1 depicts a flow diagram of an exemplary segmentation procedure in accordance with one exemplary embodiment of the present invention. Such segmentation can use attenuation, 3-dimensional connectivity and presences of edges to separate one anatomical body from another. For example, in step 102, 3-dimensional volumetric data of the head or another anatomical part (e.g., the colon) may be represented as a 3D voxel array using conventional MRI techniques so as to obtain an image, as it is know in the art. The voxels may be comprised of 16-bit data segments (but may be used for any bit depth). In step 104, the image obtained in step 102 may be resampled to make the voxels isotropic, e.g., thereby correcting the image. Isotropy refers to the resolution of the modified volume that can be identical or substantially similar along each of the X, Y, and Z axes. One of the purposes of step 104 is to improve the behavior of subsequent erosion and growth operations (as discussed herein with reference to steps 116 and 124). Isotropy can also generally simplify the computation of image edges and improve morphology operation.

For example, in step 106, the isotropic volume, containing the result of the isotropy correction procedure of step 104 as voxels, may be provided or determined. In step 108, the core (e.g., of the brain, colon, etc.) may be extracted. For example, the voxels obtained in step 106 may be subjected to preliminary thresholding using a soft tissue (or brain tissue) attenuation range $[C_{min}, C_{max}]$. With respect to imaging the brain, these parameters describe the range of a tissue signal which may be reliably obtained by specifying the seed area(s) within periventricular white matter. (The optional specification of the white matter seed may be the only manual procedure performed by the operator.) When imaging colon, these parameters aim to create the Core set, i.e., an over-inclusive soft tissue volume that contains the colon, colon folds, colorectal polyps and tumors. For example, the Core excludes the bulk of tagged FM material but not untagged FM. The signal intensity of the white matter may be averaged to yield $S_w$. Then, the brain tissue attenuation range $[C_{min}, C_{max}]$ may be obtained using the following exemplary equation:

$C_{min} = S_w * \text{LowThreshold}$, $C_{max} = S_w * \text{HighThreshold}$.

Exemplary unbiased values based on phantom experiments, for common T1-weighted MR sequence, may be 0.55 for the LowThreshold and 1.30 for the HighThreshold. These exemplary thresholds may assure an inclusion, for visualizing the brain, of all parts of the cerebral gray and white matter. This range excludes the fluid, some fat, and air. However, soft tissue (such as muscle, skin, and blood vessels) may be included in this preliminary core set.

In step 110, the results of step 108 may be represented as a binary volume. For example, all voxels with intensities between $C_{min}$ and $C_{max}$ may be assigned a value of "1", while all others outside this range are assigned a value "0."

Figure 3:
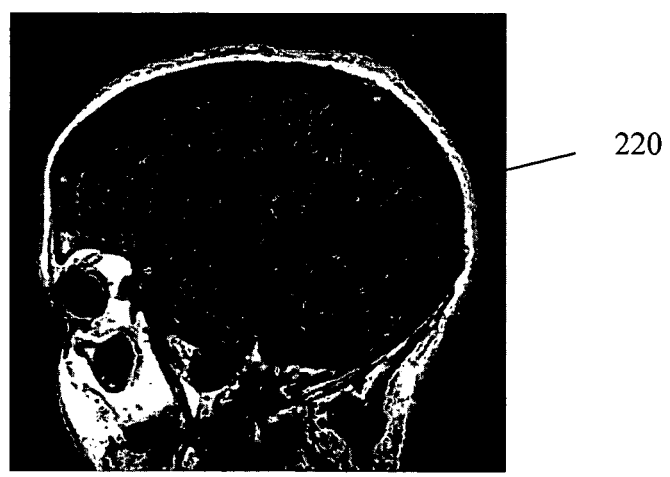
FIG. 3 is a cross-sectional view of 3-dimensional edges, superimposed on the T1-weighted MRI of FIG. 2 generated using a software arrangement, system and/or method according to the present invention.

In step 112, an edge detection of 3-dimensional edges of the isotropic volume of the structure obtained in step 106 may be performed. The algorithm for accomplishing this may be a Canny 3D edge detector described above, and/or a variant thereof. Free parameters involved in such task may be previously described are $\sigma$ and $H_{min}$-threshold for edge strength, e.g., Smoothing Kernel=exp $(-R^2/2*\sigma^2)$. FIG. 3 illustrates the edges of an image 220 on a subject extracted using parameters $\sigma=1.0$ voxel, and $H_{min}=0.04$. Since edges correspond to changes in the magnetic resonance signal across neighboring voxels, the edges can be successfully represented "as voxel surfaces" or facets. This representation has a desirable property of assigning e.g., no volume to the edge set. For example, edges are generally singularities between regions. The values inside the edges are not defined, and may not necessarily be reliably used. For 0-thickness edges such a problem generally may not exist, for voxel based edges, half of the image may be undefined. This can be done using a variant of Canny 3D edge detector, as described in O. Monga, et al. "Recursive filtering and edge tracking: two primary tools for 3-D edge detection," Image and Vision Computing 4(9): 203-214; 1991. Free parameters involved in this task are: smoothing kernel size $\sigma$, and $H_{min}$, the magnitude of the edges considered significant for the task of detecting the interface between the target structures (e.g., brain or colon).

In step 114, the results of step 112 may be represented as a binary volume. If a 3 dimensional edge is present, e.g., at its surface, a value of "1" may be assigned. If not, a value of "0" may be assigned. In this manner, edge vertexes are obtained.

In step 116, an exemplary procedure according to an exemplary embodiment of the present invention in which the initially detected edges are subtracted from the Core occurs. This step may assist in separating anatomically distinct but spatially adjacent tissues. For example, with reference to imaging the colon, such separation would be between untagged FM and the colon wall. When imaging the brain, the connections between the brain and non-brain tissue may be referred to as "bridges." Then, in step 118, an erosion takes place, in which surface voxels (likely, vertices) of, e.g., the Core are morphologically eroded similarly as described in L. Vincent. Mathematical morphology and its applications to image and signal processing. Kluwer Academic Publishers, 2000. J. Goutsias and D. Bloomberg, Eds. It should be noted that distinct regions need not be fully separated for the final result to be successful—an independent erosion process will contribute to the separation of adjacent tissue. Initial Core Surface is defined as a combination of boundary voxels (likely, vertices) and edge surface. Boundary voxels are those Core voxels that contain at least one non-core voxel (likely, vertices) in their 26-neighbor vicinity. Edge surface is constructed from Edge vertexes obtained from step 114.

Figure 2:
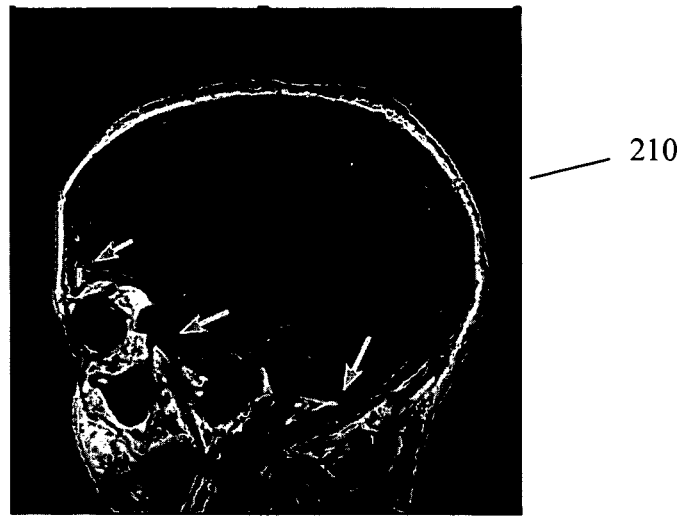
FIG. 2 is a cross sectional view through an exemplary core set superimposed on a T1-weighted brain image using Magnetic Resonance Imaging ("MRI")
Figure 4:
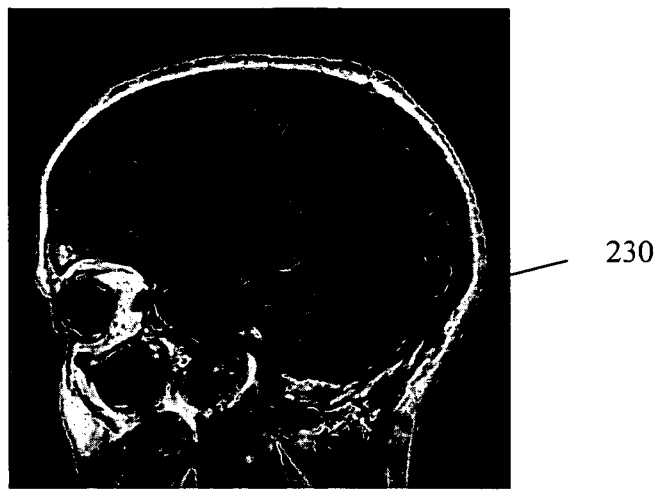
FIG. 4 is an exemplary image of an eroded set from FIG. 2 after the erosion.

An isotropic wavefront may begin to propagate from such Core Surface advancing only through present Core voxels (likely, vertices). The Core voxels (likely, vertices) passed by the wavefront within one time unit (preferably, the clock ticks at the fractions of time units i.e. 0.1 tu (time unit), to facilitate subvoxel precision described below) may be recorded and marked as "PEELED", and the Core Surface may be updated. Such operation may be repeated P times, where P is another empirically derived parameter of the system. For example, with reference to the scan of the brain, P should exceed the maximum width of the bridges that connect the brain to other tissues. The speed of the wavefront may be such that in one time unit, the wavefront can traverse the linear dimension of one voxel. However, a user may specify an arbitrary or predetermined peeling time P, such as 3.5. This may allow for a greater control in achievable tissue segmentation. Further, wavefront is preferably propagated through voxel vertexes, and not via voxels. This configuration allows the resolution of certain edge-related contradictions that may not be achievable using conventional voxel propagation models, as described above. FIG. 4 shows an exemplary image 230 of a sample set obtained based on an image 210 of FIG. 2 after the erosion procedure of step 118 with P=3.5.

For example, erosion may result in a number of connected components that are all identified and ordered by size. The maximum (largest volume) component, called ErodedCore, with reference to imaging the patients colon may, consist of all components, including patient's abdomen and pelvis, the colon walls and polyps. Other connected components may consist of FM that is not attached to the colon. Additional characteristics such as orientation, attenuation histogram, texture, or shape may be computed and tested to potentially improve accuracy.

Figure 5:
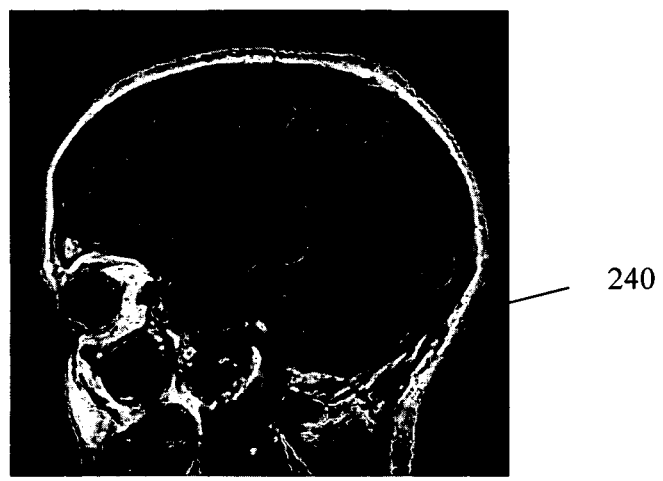
FIG. 5 is an exemplary image of an exemplary maximum connected component of the peeled set.

In step 120, the connected components or maximal components may be obtained, e.g., identified and ordered by size. For imaging the brain, an assumption may be made that the maximum component ("MCC") (e.g., having the largest volume) may consist exclusively of the patient's brain (as depicted in an image 240 in FIG. 5). The other components may include other elements such as the eye nerve, etc. Each component may be processed separately to calculate its volume. All other components may be labeled as "OTHER," for example. It should be understood that the same or similar procedure can be performed when imaging the colon.

In step 122, the connected components may be labeled. Each component may be assigned a volume and several shape characteristics, and may also be represented as a binary object. In this manner, the connected components are constructed.

In step 124, the MCC and OTHER connected components may be grown separately but simultaneously to offset the morphological erosion of original tissue done in step 116. Initial surface may be constructed from present core voxels that have at least one "PEELED" voxel within the 26-neighbor vicinity, which may allow for a better approximation of spherical wavefront than 8-neighbour model. Surface voxels may be grown using spherical wavefront propagation, with parameter G representing the growth time measured in the linear dimension of a voxel. Those voxels determined to be "PEELED" in step 116 may be added back to each component. Upon adding of such voxels, the label of each added voxel may be changed back to "CORE" or "OTHER." Additional, the growth may be constrained by the 3D edges of step 114 (e.g., the wavefront would likely not be permitted to cross the edge surface).

Figure 6:
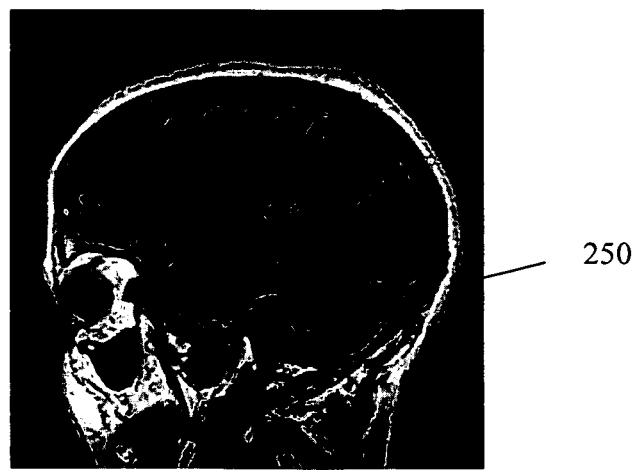
FIG. 6 is an exemplary image of an exemplary maximal set after a constrained growth.

In step 126, a final mask may be provided. This can be done by having, e.g., all voxels that have a "CORE" tag after completion of step 124 may be assigned a value of "1" while all others may be assigned a value of "0." FIG. 6 depicts an image 250 having a maximal set after a constrained growth with G=7.0.

For example, the "growth" procedure and the use of masks can be additionally explained as follows. The exemplary embodiment of the software arrangement, system and method of the present invention "grows" each connected component, including the Eroded Core, to offset the morphological erosion of original tissue. Surface voxels can be grown using a wavefront propagation algorithm. It is possible to add back to each component only those voxels that belonged to the original Core. The results of the morphological growing are preferably masks for separate connected bodies. The largest body may be called Final Core. When imaging the colon bodies other than Final Core presumably comprise FM. These bodies are electronically removed, i.e., set to the attenuation of the air.

Exemplary embodiments of the present invention can utilize a number of free parameters that may be adjusted; when imaging the colon, to avoid removal of normal colonic anatomy (interhaustral folds, ileo-cecal valves, or polyps). It is preferable to err strictly on the side of under-segmentation. Therefore, a removal of significant sized colorectal polyps may be avoided.

Exemplary Procedure of the Present Invention

Provided below is the pseudo-code for a particular part of the Peel/Grow Process. This exemplary part represents the formation of the new generation in the wavefront (Son Generation) given the current generation (Father).

For example, the wavefront is represented by the stack. The element of the stack are represented by the following structure. All the elements on the stack constitute the snapshot of the wavefront between 2 consecutive ticks of the times

```
typedef struct {
        INT32       offs;      // Absolute offset of the element in the
                               // LabelMatrix
        WORD16      age;       Age of the element, measured in Timer Ticks
                               // from the beginning of propagation.
} WCELL,*LPWCELL;
void    AddNextGeneration(
        BYTE        TAG,           //Unmarked Label Value
                                   //represents all the vertexes where
                                   //the wavefront could be
                                   //propagated.
        BYTE        SUB,           //Mark Label is assigned to vertexes
                                   //that are reached by Wavefront
        LPWCELL&    Stack,         //Stack of vertexes descriptions
                                   //representing the waveffront
        LPWCELL&    Son,           //Top element of the Stack
        int         Timer )        //Upper time limit for the vertexes
                                   //to join the new generation of the
                                   //wavefront. It is supplied by the external
                                   //counter
{
Calculate the length of the Current Wavefront generation
int NumbefFathers = Son-Stack;
        // Perform the loop for every father trying to attach all possible Sons
        for ( int i=0; i<NumberFathers; i++ ) {
                int     FatherOffs   = Stack[i].offs;
                int     FatherAge    = Stack[i].age;
                int     MaxDirTime   = Timer-FatherAge;
                // Try to connect each of the 26 directions
                for ( int outdir=0; outdir<26; outdir++ ) {
                        // Calculate absolute offset of the potential son
                        // inside the LabelMatrix.
                        int offs    = FatherOffs + m_SonOffs[outdir];
                        // Skip the Edge Vertexes.
                        if ( !IsEdgeVertex( offs ) &&
                        // Check if allowed to propagate into this son
                        LabelMatx[offs]==TAG      &&
                        // Check that enough time to propagate
                        DirTime[outdir]<=MaxDirTime )
                        // Put this son on the Stack. Importantly, // // Note that
                        // each vertex could be put on the stack by // // several fathers
                        // since we do not change thee label of the son // yet. This results in
                        the duplicated vertexs // on the stack
                                {
                                Son->offs = offs;
                                Son->age = FatherAge+DirTime[outdir];
                                Son++;
                                }
                }
        }
Get total number of new sons
int     NumberSons = (Son-Stack)-NumFather;
```

This exemplary procedure can remove all the duplicated sons from the stack. From all duplicated identical sons, the son with the youngest age is preserved on the stack and marked as the SUB in the Matrix.

NumberSons=RemoveAllDuplicatedSons(Son,NumberSons);

Only fathers that still could propagate, should be preserved on the stack. They become additional sons.

```
Son = Stack;
for ( int i=0; i<NumFather; i++ ) {
        LPBYTE Father    = LabelMatx+Stack[i].offs;
        Get the maximal allowed timer value for all further generations.
        WORD32 MaxDirTime   = MaxAllowedTimer-Stack[i].age;
    Try to connect each of the 26 directions
        for ( int outdir=0; outd<26; outdir++ )
            if ( Father[m__SonOffs[outdir]]==TAG && DirTime[outdir]<=MaxDirTime )
                { *Son++ = Stack[i]; break; }
}
Now copy the new generation
memcpy( Son,Stack+NumFather,NumSon*sizeof(*Son));
Son+= NumSon;
}
bool   AddNextGeneration(
       BYTE        TAG,               //Unmarked Label Value
                                      //represents all the voxels where //the wavefront
                                      could be //propagated.
       BYTE        SUB,               //Mark Label is assigned to voxels
                                      //that are reached by Wavefront
       LPWCELL&   Stack,              //Stack of voxels representing Wavefront
       int&       StackAllocSz,
       LPWCELL&   Son )
{
bool   res = false;
       // Put all possible allowed Sons on the stack
const int NumF = (int)(Son-Stack);
       for ( int i=0; i<NumF; i++ ) {
               const int        Foffs      = Stack[i].offs;
               const int        Fage       = Stack[i].age;
               const WORD32     MaxDirTime = m__Timer-Fage;
               xz( MaintainSufficientStack( &Stack,&StackAllocSz,&Son,NDR ));
               // Try to connect each of the NDR directions
               for ( int outd=0; outd<NDR; outd++ ) {
                   int    offs   = Foffs + m__SonOffs[outd];
                   if ( m__Mask[offs]==TAG && m__DirTime[outd]<=MaxDirTime )
                       AddWcell( Son,offs,Fage+m__DirTime[outd] );
               }
       }
       // Now sort all Sons by their age starting with the youngest
       int NumS = (int)(Son-Stack)-NumF;
       xz((SortWcellArrByAge<TAG,SUB,EDGE>( Stack+NumF,NumS )));
       // Now leave only fathers which still could propagate. They become additional sons
       Son = Stack;
       for ( int i=0; i<NumF; i++ ) {
               const LPBYTE Father= m__Mask+Stack[i].offs;
               const WORD32 MaxDirTime= m__LastTimer-Stack[i].age;
               // Try to connect each of the NDR directions
               for ( int outd=0; outd<NDR; outd++ )
                       if ( Father[m__SonOffs[outd]]==TAG &&
m__DirTime[outd]<=MaxDirTime )
                       { *Son++ = Stack[i]; break; }
       }
       // now copy the new sons
       memcpy( Son,Stack+NumF,NumS*sizeof(WCELL));
       Son+= NumS;
       res = true;
func__exit:
       return res;
}
```

Experimental Results of Imaging a Colon

Two considerations should be addresses in order for fecal segmentation to be effective. The first is the ability to remove tagged and untagged fecal material, and the second is the desire to preserve the normal colon wall as well as polyps and tumors. Initially, to determine the effective of segmentation procedure according to the present invention, it is preferable to define the ground truth. To accomplish this effort, hand drawn region of interests ("ROI") for the FM were traced manually by an experienced expert observer, as shown in FIGS. 7(*a*) and 7(*b*). FIG. 7(*a*) shows an image of a cross-section of the colon 400 in question.

Tracing was done using a locally developed program that allows the user to view the anatomy simultaneously in three orthogonal planes. Based on automatically defined colon/air interface, a ROI for colon lumen was also constructed using an elliptical region shown in FIG. 7(*b*). Axial slice of the colon are shown in these figures, dashed lines 410 indicating the hand-drawn contours defining FM and the thin line 420 indicating the colon lumen. An elliptical region of interest 430 can be defined by the operator to isolate the colon section from nearby sections.

Two error types of an exemplary embodiment of a segmentation technique according to the present invention can be measured based on the manual reference standard: i) an over-segmentation error ("OE"), and ii) an under-segmentation ("UE")—a graph 510 of which is shown in FIG. 8(*a*), and ii) an under-segmentation ("UE")—a graph 520 of which is shown in FIG. 8(*b*). OE occurs when normal colon is removed from the data and UE occurs when fecal material is not segmented from the data. Two expert observers (with knowledge of the normal appearance of the colon wall and folds) generated makes for FM and for the colon wall in each of 20 discrete colon segments ranging in length from 5-10 cm. The 20 colon segments were taken from subjects who followed a 3-meal diet, i.e., where distal untagged FM was present. The 20 segments were further characterized by the attenuation level of the residual fecal material ("FM"), the volume of the FM present, and luminal area of the colon. The colon lumen cross-sectional area ranged from 6.2 to 38.0 $cm^2$. The volume of FM in the colon segments ranged 0-12.7 $cm^3$. There was a wide range in the attenuation of FM depending on the segment. A mean attenuation per segment was determined as ranging from −78 HU (poor or no tagging) to 1287 HU.

The exemplary embodiment of the present invention involved in this experiment removed 0.14±0.24 $cm^3$ (mean±standard deviation across all sections) of colon wall, representing only 0.77%±1.25% of the luminal volume. Over-segmented voxels were arranged as a thin shell along the colon surface producing little distortion of colon folds. OE was directly related to the volume of FM (linear regression, p=0.01) as shown in FIGS. 8a and 8b. UE for sections containing FM averaged 1.2±2.1 $cm^3$. Omitting those colon segments with untagged stool (defined as having an average FM attenuation<0 HU) drastically reduced UE to 0.3±0.2 $cm^3$. UE was not correlated with lumen volume or with the volume of FM. These results are illustrated in the graphs of FIGS. 8(a) and 8(b).

For example, FIG. 8.(a) shows a graph 510 of an over-segmentation error (OE) in 20 colon segments which is directly related (p=0.01) to FM volume shown in previous figures in $cm^3$ (cc). There was a trend for OE to be inversely related to lumen size. Therefore, it is likely that the less residual fecal matter and the greater the colonic distension the less OE will occur. FIG. 8(b) shows a graph 520 of an Under-segmentation error (UE) in $cm^3$ (cc), plotted as a function of attenuation of FM. UE appears to be strongly related to FM attenuation (P<0.001).

Based on these observations the initial error analysis of the proposed algorithm is encouraging, showing minimal over-segmentation and, in spite of incomplete 3-dose barium tagging protocol, the removal of approximately 95% of FM.

Figures 9A, 9B, 9C, 9D:
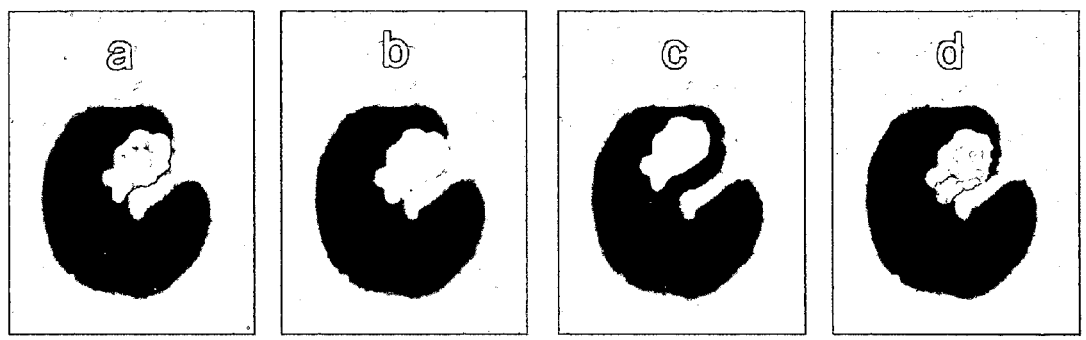
FIG. 9(a) is an exemplary image of a slice of a colon generated based on the differences between tagged FM and the colon.
FIG. 9(b) is an exemplary image of the slice of the colon of FIG. 9(a) which takes into consideration the presence of images edges.
FIG. 9(c) is an exemplary image of the slice of the colon of FIG. 9(a) which further takes into consideration a connectivity of voxels.
FIG. 9(d) is an exemplary image of the slice of the colon of FIG. 9(a) which takes into consideration the presence of images edges and the connectivity of voxels

As a further proof of the benefits of the exemplary embodiments of the software arrangement, system and method according to the present invention, FIGS. 9(a)-9(d) show the progressive improvement of the visualization of the same colon. In particular, FIG. 9(a) shows the image of a slice of an exemplary colon of a patient that was generated using conventional algorithms that utilize attenuation differences between the tagged FM and colon. The image is progressively improved when it is generated also based on image edges (see FIG. 9(b)) and a connectivity between the voxels according to the exemplary embodiment of the present invention. FIG. 9(d) illustrates the resultant image when both the edges and connectivity are taken in consideration.

Further Experimental and Comparative Results when Imaging Colon

Figures 10A, 10B, 10C:
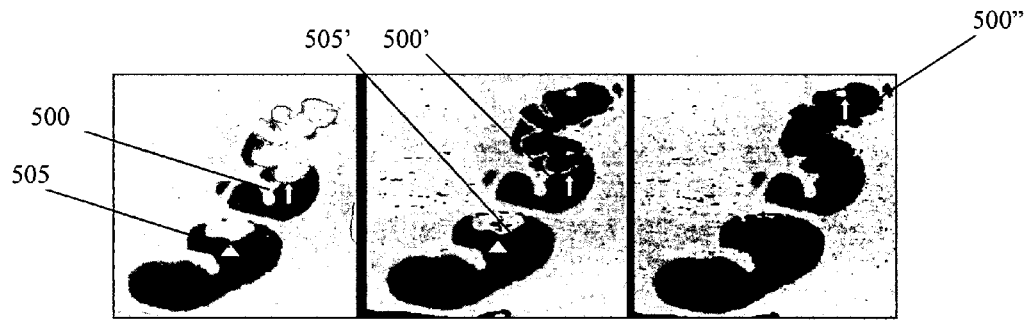
FIG. 10(a) is an exemplary image of an axial CTC slice of a patient produced by conventional techniques.
FIG. 10(b) is the exemplary image of the slice shown in FIG. 10(a) generated by a threshold-based algorithm.
FIG. 10(c) is the exemplary image of the slice shown in FIG. 10(a) generated by the exemplary embodiment of the software arrangement, system and method according to the present invention.

As discussed above, conventional CTC techniques require bowel cleansing for optimal detection of colorectal polyps. If accurate detection of clinically significant colon lesions could be performed without the need for bowel cleansing, patient acceptance of screening would significantly increase. While the results using such techniques appear to be promising, residual untagged fecal material ("FM") often remains within the colon. FIG. 10(a) shows an exemplary image of an axial CTC slice of in a patient who underwent barium tagging, without bowel cleansing. Partially tagged fecal material 500 and untagged fecal material 505 is illustrated in this drawing.

FIG. 10(b) shows the results obtained with a simple threshold-based algorithm ("TBA"). Referring to the upper part of this image, even though most of the tagged FM was correctly removed, the voxels located near the boundary of the FM and gas were not segmented 500'. The attenuation of these voxels is similar to that of the colon wall, causing the relative failure of TBA. The attenuation of such "FM-AIR surface" voxels is lower than the nearby tagged FM due to the partial volume effect. The fecal material in the lower part of the image 505' was not optimally tagged with the barium and has an attenuation close to that of the colonic wall. TBA does not segment this untagged fecal matter.

FIG. 10(c) shows the image of the same colon section after the use of the exemplary embodiment of the software arrangement, system and method according to the present invention which was effective in removing the fecal material. As shown in this image, the residual FM 500" is significantly reduced. Indeed, this exemplary embodiment addressed the deficiencies prevalent in the conventional TBA systems. A preliminary clinical quantitative study demonstrated that our algorithm successfully removes 95% of FM while erroneously removing 0.77% of non-critical colon voxels. The morphological analysis of the BB software helps to remove the residual FM-Air surface voxels. For the second problem, related to the untagged FM, a 3D surface edge detector combined with connectivity analysis allows the morphological module to remove the untagged fecal material almost completely. Despite these techniques, a small amount of untagged FM remains in the colon (arrow).

Indeed, it is possible to address the existing problems with the conventional techniques by implementing an exemplary Texture Based 3D Edge Detection technique according to the present invention. The exemplary embodiment of the present invention can be implemented using visual tools (graphical user interfaces) that may be used by conventional computers. This would allow clinicians to use the software arrangement, system and method according to the present invention without upgrading their hardware.

Applications of the exemplary embodiments of the present invention may be implemented as a software program, either directly by the computer controlling the imaging system or by a separate computer.

The foregoing merely illustrates the principles of the invention. Various modifications and alterations to the described embodiments will be apparent to those skilled in the art in view of the teachings herein. For example, the aforementioned approaches may be used to image other parts of the body or may be used with other imaging technologies. It will thus be appreciated that those skilled in the art will be able to devise numerous systems and methods which, although not explicitly shown or described herein, embody the principles of the invention and are thus within the spirit and scope of the invention. All publications cited above are incorporated herein by reference in their entireties.

What is claimed is:

1. A system for generating an image of at least one portion of an anatomical structure, comprising:
    a processing arrangement which is programmed to:
        receive first image data;
        generate second image data based at least partially on the first image data using a peel procedure with a subvoxel precision;
        generate third image data based at least partially on the first image data using a grow procedure with a subvoxel precision, wherein the grow procedure is based on surface voxels and connected voxel components which are associated with the surface voxels, wherein the generation of the third image is provided so as to offset processing of the surface voxels associated with the at least one portion;

compare the second image data with the third image data to obtain fourth image data so as to separate anatomically distinct and adjacent sections of the at least one portion from one another; and generate the image based on the fourth image data.

2. The system according to claim 1, wherein the third data is associated with a volume of a soft tissue of at least one portion of the anatomical structure based on the first image data.

3. The system according to claim 1, wherein the surface voxels are eroded morphologically, and wherein the connected voxel components are ordered according to sizes thereof.

4. The system according to claim 1, wherein the voxel components are grown using a wavefront propagation technique.

5. The system according to claim 1, wherein the processing arrangement is further programmed to add voxels that are part of the third data to the voxel components.

6. The system according to claim 1, wherein the processing arrangement is further programmed to generate data masks for separate connected bodies of the at least one portion, and to remove the connected bodies that are smaller in size than a predetermined threshold so as to provide at least one resultant body.

7. The system according to claim 6, wherein the image is generated further based on the at least one resultant body.

8. The system according to claim 1, wherein the processing arrangement is further programmed to:

generate further data associated with a volume of a soft tissue of at least one portion of the anatomical structure based on the first image data; and process information associated with an erosion of the surface voxels so as to generate the connected voxel components.

9. The system according to claim 1, wherein at least one of the first image data or the second, image data includes information regarding voxels, and wherein the voxels are isotropic.

10. The system according to claim 1, wherein at least one of the first image data or the second image data includes information regarding surface voxels.

11. The system according to claim 1, wherein the at least one of the grow procedure or the peel procedure comprises a propagation procedure.

12. The system according to claim 1, wherein the at least one of the grow procedure or the peel procedure comprises a wavefront propagation procedure, and wherein the wavefront propagates in a three-dimensional space in at least one predefined direction with respect to a surface.

13. The system according to claim 1, wherein the at least one of the grow procedure or the peel procedure comprises a spherical wavefront propagation procedure.

14. The system according to claim 1, wherein at least one of the first image data or the second image data include information regarding voxels, and the at least one of the grow procedure or the peel procedure is based on at least one of a growth time or a peel time that is measured in a linear dimension of at least one of the voxels.

15. The system according to claim 1, wherein at least one of the first image data or the second image data include information regarding voxels, and at least one of (i) a growth time is measured on a scale including fractional time-units to provide for subvoxel measurements, or (ii) a peel time is measured on a scale including fractional time-units to provide for subvoxel measurements.

16. The system according to claim 1, wherein at least one of the first image data or the second image data include information regarding voxel vertices, and the at least one of (i) the grow procedure is performed at least one of on the voxel vertices or through the voxel vertices or (ii) the peel procedure is performed at least one of on the voxel vertices or through the voxel vertices.

17. The system according to claim 1, wherein the at least one of the grow procedure or the peel procedure is constrained by at least one constraint associated with at least one edge related to the first image data.

18. The system according to claim 1, wherein at least one of the first image data or the second image data include information regarding voxels, and the at least one of the grow procedure or the peel procedure is constrained by a set of the voxels.

19. The system according to claim 18, wherein the set of the voxels comprise a core set of voxels.

20. The system according to claim 19, wherein the core set comprises two colors, and a first of the two colors is black and a second of the two colors is white.

21. The system according to claim 19, wherein the core set is generated based on at least one of a signal intensity associated with the voxels or a luminance associated with the voxels.

22. The system according to claim 19, wherein the second image data comprises data associated with at least one segment of a segmentation associated with the first image data, wherein the segment is based at least partially on the core set, and the at least one of the grow procedure or the peel procedure is constrained by the core set.

23. The system according to claim 1, wherein at least one of the first image data or the second image data includes information regarding a maximum connected component ("MMC"), and the at least one of the grow procedure or the peel procedure is performed on the MMC.

24. The system according to claim 1, wherein the at least one of the grow procedure or the peel procedure is performed using at least one of an 8-neighbor model or a 16-neighbor model.

25. A non-transitory computer-accessible medium for generating an image of at least one portion of an anatomical structure, which comprises instruction stored thereon that comprise:

a first set of instructions, which when executed by a hardware processing arrangement, configure the processing arrangement to receive first image data;

a second set of instructions, which when executed by the processing arrangement, configure the processing arrangement to generate second image data based at least partially on the first image data using a peel procedure with a subvoxel precision; and a third set of instructions, which when executed by the processing arrangement, configure the processing arrangement to generate third image data based at least partially on the second image data using a grow procedure with subvoxel precision, wherein the grow procedure is based on surface voxels and connected voxel components which are associated with the surface voxels, wherein the generation of the third image is provided so as to offset processing off the surface voxels associated with the at least one portion; and a fourth set of instructions, which when executed by the processing arrangement, configure the processing arrangement to generate the image based on the third image data and the second image data.

26. The computer-accessible medium according to claim 25, further comprising a fourth set of instructions, which when executed by the processing arrangement, configure the processing arrangement to at least one of display or store the image in a storage arrangement in at least one of a user-accessible format or a user-readable format.

27. The computer-accessible medium according to claim 25: wherein
the third image data is associated with a volume of a soft tissue of the at least one portion of the anatomical structure based on the first image data; and
the processing arrangement is further configured to compare the second image data with the third data to obtain fourth data so as to separate anatomically distinct and adjacent sections of the at least one portion from one another, wherein the generation of the image is further based on the fourth data.

28. The computer-accessible medium according to claim 27, further comprising additional instructions, which when executed by the processing arrangement, further configure the processing arrangement to:
generate data masks for separate connected bodies of the at least one portion; and
remove the connected bodies that are smaller in size than a predetermined threshold so as to provide at least one resultant body.

29. The computer-accessible medium according to claim 25, wherein at least one of the first image data or the second image data include information regarding voxels, and at least one of (i) a growth time is measured on a scale including fractional time units to provide for subvoxel measurements, or (ii) a peel time is measured on a scale including fractional time-units to provide for subvoxel measurements.

30. The computer-accessible medium according to claim 25, wherein at least one of the first image data or the second image data include information regarding voxels, a set of the voxels comprise a core set of voxels, the second image data comprises data associated with at least one segment of a segmentation associated with the first image data, the segment is based at least partially on the core set, and the at least one of the grow procedure or the peel procedure is constrained by the core set.

31. The computer-accessible medium according to claim 25, wherein at least one of the first image data or the second image data includes information regarding a maximum connected component ("MMC"), and the at least one of the grow procedure or the peel procedure is performed on the MMC.

32. A method for generating an image, comprising:
receiving first image data;
generating second image data based at least partially on the first image data using a peel procedure with a subvoxel precision;
generating third image data based at least partially on the second image data using a grow procedure with a subvoxel precision, wherein the grow procedure is based on surface voxels and connected voxel components which are associated with the surface voxels, wherein the generation of the third image is provided so as to offset processing of the surface voxels associated with the at least one portion; and using a processing arrangement, generating the image based on the third image data and the second image data, wherein the processing arrangement includes at least one hardware processor.

33. The method according to claim 32, further comprising at least one of displaying or storing the image in a storage arrangement in at least one of a user-accessible format or a user-readable format.

34. The method according to claim 32, wherein,
the third data is associated with a volume of a soft tissue of at least one portion of an anatomical structure based on the first image data;
the second image data is compared with the third image data to obtain fourth image data so as to separate anatomically distinct and adjacent sections of the at least one portion from one another.

35. The method according to claim 34, further comprising:
generating data masks for separate connected bodies of the at least one portion; and
removing the connected bodies that are smaller in size than a predetermined threshold so as to provide at least one resultant body.

36. The method according to claim 32, wherein at least one of the first image data or the second image data include information regarding voxels, and at least one of (i) a growth time is measured on a scale including fractional time-units to provide for subvoxel measurements, or (i) a peel time is measured on a scale including fractional time-units to provide for subvoxel measurements.

37. The method according to claim 32, wherein at least one of the first image data or the second image data include information regarding voxels, a set of the voxels comprise a core set of voxels, the second image data comprises data associated with at least one segment of a segmentation associated with the first image data, the segment is based at least partially on the core set, and the at least one of the grow procedure or the peel procedure is constrained by the core set.

38. The method according to claim 32, wherein at least one of the first image data or the second image data includes information regarding a maximum connected component ("MMC"), and the at least one of the grow procedure or the peel procedure is performed on the MMC.

39. A system for generating an image, comprising:
a processing arrangement which is programmed to:
receive first image data;
generate second image data based at least partially on the first image data using a peel procedure with a subvoxel precision which is based at least in part on a fractional number of peels;
generate third image data based at least partially on the second image data using a grow procedure with a subvoxel precision, wherein the grow procedure is based on surface voxels and connected voxel components associated with the surface voxels; and
generate the image based on the third image data and the second image data, wherein at least one of the third image data or the second image data include information regarding voxels, and the fractional number of peels is associated with a scale facilitating subvoxel measurements.

40. The system according to claim 39, wherein at least one of the first image data or the second image data include information regarding voxel vertices, and the peel procedure is performed at least one of (i) on the voxel vertices or (ii) through the voxel vertices.

41. A non-transitory computer-accessible medium for generating an image, which comprises instruction stored thereon that comprise:
- a first set of instructions, which when executed by a hardware processing arrangement, configure the processing arrangement to receive first image data;
- a second set of instructions, which when executed by the processing arrangement, configure the processing arrangement to generate second image data based at least partially on the first image data using a peel procedure with subvoxel precision which is based at least in part on a fractional number of peels;
- a third set of instructions, which when executed by the processing arrangement, configure the processing arrangement to generate third image data based at least partially on the second image data using a grow procedure with a subvoxel precision, wherein the grow procedure is based on surface voxels and connected voxel components associated with the surface voxels; and
- a fourth set of instructions, which when executed by the processing arrangement, configure the processing arrangement to generate the image based on the first image data and the second image data, wherein at least one of the first image data or the second image data include information regarding voxels, and the fractional number of peels is associated with a scale facilitating subvoxel measurements.

42. The computer-accessible medium according to claim 41, wherein at least one of the first image data or the second image data include information regarding voxel vertices, and the peel procedure is performed at least one of (i) on the voxel vertices or (ii) through the voxel vertices.

43. A method for generating an image, comprising:
receiving first image data;
generating second image data based at least partially on the first image data using a peel procedure with subvoxel precision which is based at least in part on a fractional number of peels;
generating third image data based at least partially on the second image data using a grow procedure with a subvoxel precision, wherein the grow procedure is based on surface voxels and connected voxel components associated with the surface voxels; and
using a processing arrangement, generating the image based on the first data and the second data, wherein the processing arrangement includes at least one hardware processor, and wherein at least one of the first image data or the second image data include information regarding voxels, and the fractional number of peels is associated with a scale facilitating subvoxel measurements.

44. The method according to claim 43, wherein at least one of the first image data or the second image data include information regarding voxel vertices, and the peel procedure is performed at least one of (i) on the voxel vertices or (ii) through the voxel vertices.

45. A system for generating an image, comprising:
a processing arrangement which is programmed to:
receive first image data;
generate second image data based at least partially on the first image data using a grow procedure with a subvoxel precision;
generate third data based at least partially on the second image data using a grow procedure with a subvoxel precision, wherein the grow procedure is based on surface voxels and connected voxel components associated with the surface voxels; and
generate the image based on the first image data and the second image data, wherein at least one of the first image data or the second image data include information regarding voxels, and at least one of (i) a growth time is measured on a scale including fractional time-units to provide for subvoxel measurements, or (ii) a peel time is measured on a scale including fractional time-units to facilitate subvoxel measurements.

46. The system according to claim 45, wherein at least one of the first image data or the second image data include information regarding voxel vertices, and the at least one of (i) the grow procedure is performed at least one of on the voxel vertices or through the voxel vertices, or (ii) the peel procedure is performed at least one of on the voxel vertices or through the voxel vertices.

47. A non-transitory computer-accessible medium for generating an image, which comprises instruction stored thereon that comprise:
- a first set of instructions, which when executed by a hardware processing arrangement, configure the processing arrangement to receive first image data;
- a second set of instructions, which when executed by the processing arrangement, configure the processing arrangement to generate second image data based at least partially on the first image data using a grow procedure with a subvoxel precision;
- a third set of instructions, which when executed by the processing arrangement, configure the processing arrangement to generate third image data based at least partially on the second image data using a grow procedure with a subvoxel precision, wherein the grow procedure is based on surface voxels and connected voxel components associated with the surface voxels; and
- a fourth set of instructions, which when executed by the processing arrangement, configure the processing arrangement to generate the image based on the first image data and the second image data, wherein at least one of the first image data or the second image data include information regarding voxels, and at least one of (i) a growth time is measured on a scale including fractional time-units to provide for subvoxel measurements, or (ii) a peel time is measured on a scale including fractional time-units to facilitate subvoxel measurements.

48. The computer-accessible medium according to claim 47, wherein at least one of the first image data or the second image data include information regarding voxel vertices, and the at least one of (i) the grow procedure is performed at least one of on the voxel vertices or through the voxel vertices, or (ii) the peel procedure is performed at least one of on the voxel vertices or through the voxel vertices.

49. A method for generating an image, comprising:
receiving first image data;
generating second image data based at least partially on the first image data using a grow procedure with subvoxel precision;
generating third image data based at least partially on the second image data using a grow procedure with a subvoxel precision, wherein the grow procedure is based on surface voxels and connected voxel components associated with the surface voxels; and
using a processing arrangement, generating the image based on the first data and the second data, wherein the processing arrangement includes at least one hardware processor, and wherein at least one of the first image data or the second image data include information regarding voxels, and at least one of (i) a growth time is measured on a scale including fractional time-units to provide for subvoxel measurements or (ii) a peel time is measured on a scale including fractional time-units to facilitate subvoxel measurements.

50. The method according to claim 49, wherein at least one of the first image data or the second image data include information regarding voxel vertices, and the at least one of (i) the grow procedure is performed at least one of on the voxel vertices or through the voxel vertices, or (ii) the peel procedure is performed at least one of on the voxel vertices or through the voxel vertices.

51. A system for generating an image of at least one portion of an anatomical structure image, comprising:
a processing arrangement which programmed to:
receive first image data;
generate second image data based at least partially on the first image data using a peel procedure with a subvoxel precision;
generate third image data based at least partially on the second image data using a grow procedure with the subvoxel precision, wherein the grow procedure is based on at least one connected voxel component of the first image data; and
generate the image based on the second image data and the third image data.

52. The system of claim 51, wherein the at least one connected voxel component is based on surface voxels, and wherein the surface voxels are eroded morphologically, and wherein the connected voxel components are ordered according to sizes thereof.

53. The system according to claim 51, wherein the processing arrangement is further programmed to generate data masks for separate connected bodies of the at least one portion of the anatomical structure, and to remove the connected bodies that are smaller in size than a predetermined threshold so as to provide at least one resultant body.

54. The system according to claim 51, wherein at least one of the grow procedure or the peel procedure comprises a propagation procedure.

55. The system of claim 51, wherein at least one of the grow procedure or the peel procedure comprises a wavefront propagation procedure, and wherein the wavefront propagates in a three-dimensional space in at least one predefined direction with respect to a surface.

56. The system of claim 51, wherein at least one of the first image data or the second image data includes information regarding a maximum connected component ("MMC"), and at least one of the grow procedure or the peel procedure is performed on the MMC.

57. A non-transitory computer-accessible medium for generating an image of at least one portion of an anatomical structure, which comprises instruction stored thereon that comprise:
a first set of instructions which when executed by a hardware processing arrangement, configure the processing arrangement to receive first image data;
a second set of instructions, which when executed by a hardware processing arrangement, configure the processing arrangement to generate second image data based at least partially on the first image data using a peel procedure with a subvoxel precision;
a third set of instructions, which when executed by a hardware processing arrangement, configure the processing arrangement to generate third image data based at least partially on the second image data using a grow procedure with the subvoxel precision, wherein the grow procedure is based on at least one connected voxel component of the first image data; and
a fourth set of instructions, which when executed by a hardware processing arrangement, configure the processing arrangement to generate the image based on the second image data and the third image data.

58. The non-transitory computer-accessible medium of claim 57, wherein the at least one connected voxel component is based on surface voxels, and wherein the surface voxels are eroded morphologically, and the connected voxel components are ordered according to sizes thereof.

59. The non-transitory computer-accessible medium according to claim 57, further comprising a fifth set of instructions, which when executed by a hardware processing arrangement, configure the processing arrangement to generate data masks for separate connected bodies of the at least one portion of the anatomical structure, and to remove the connected bodies that are smaller in size than a predetermined threshold so as to provide at least one resultant body.

60. The non-transitory computer-accessible medium according to claim 57, wherein at least one of the grow procedure or the peel procedure comprises a propagation procedure.

61. The non-transitory computer-accessible medium of claim 57, wherein at least one of the grow procedure or the peel procedure comprises a wavefront propagation procedure, and wherein the wavefront propagates in a three-dimensional space in at least one predefined direction with respect to a surface.

62. The non-transitory computer-accessible medium of claim 57, wherein at least one of the first image data or the second image data includes information regarding a maximum connected component ("MMC"), and at least one of the grow procedure or the peel procedure is performed on the MMC.

63. A method for generating an image of at least one portion of an anatomical structure, comprising
receiving first image data;
generating second image data based at least partially on the first image data using a peel procedure with a subvoxel precision;
generating third image data based at least partially on the second image data using a grow procedure with the subvoxel precision, wherein the grow procedure is based on at least one connected voxel component of the first image data; and
using a processing arrangement, generating the image based on the second image data and the third image data, wherein the processing arrangement includes at least one hardware processor.

64. The method of claim 63, wherein the at least one connected voxel component is based on surface voxels, and wherein the surface voxels are eroded morphologically, and the connected voxel components are ordered according to sizes thereof.

65. The method of claim 63, further comprising generating data masks for separate connected bodies of the at least one portion of the anatomical structure, and to remove the connected bodies that are smaller in size than a predetermined threshold so as to provide at least one resultant body.

66. The method of claim 63, wherein at least one of the grow procedure or the peel procedure comprises a propagation procedure.

67. The method of claim 63, wherein at least one of the grow procedure or the peel procedure comprises a wavefront propagation procedure, and wherein the wavefront propagates in a three-dimensional space in at least one predefined direction with respect to a surface.

68. The method of claim 63, wherein at least one of the first image data or the second image data includes information regarding a maximum connected component ("MMC"), and at least one of the grow procedure or the peel procedure is performed on the MMC.

69. A system for generating an image of at least one portion of an anatomical structure, comprising:
a processing arrangement which is programmed to:
   receive first image data;
   generate second image data based at least partially on the first image data using at least one of (i) a grow procedure with a subvoxel precision or (ii) a peel procedure with a subvoxel precision;
   generate third data associated with a volume of a soft tissue of the least one portion based on the first image data, the third image data including information regarding surface voxels associated with the at least one portion;
   process data associated with the surface voxels so as to generate connected voxel components, and grow the connected voxel components so as to offset processing of the surface voxels associated with the at least one portion;
   compare the second image data with the third data to obtain fourth data so as to separate anatomically distinct and adjacent sections of the at least one portion from one another; and
   generate the image based on the first image data, the second image data, the fourth data and the connected voxel components.

* * * * *